United States Patent
Forsythe

(10) Patent No.: US 10,018,533 B2
(45) Date of Patent: Jul. 10, 2018

(54) QUICK CONNECT TESTING JIG

(71) Applicant: Toyota Motor Engineering & Manufacturing North America, Inc., Erlanger, KY (US)

(72) Inventor: Solomon J. Forsythe, Richmond, KY (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 479 days.

(21) Appl. No.: 14/722,305

(22) Filed: May 27, 2015

(65) Prior Publication Data
US 2016/0348820 A1     Dec. 1, 2016

(51) Int. Cl.
| | |
|---|---|
| *F01N 11/00* | (2006.01) |
| *F16L 37/08* | (2006.01) |
| *G01M 15/10* | (2006.01) |
| *G01N 1/22* | (2006.01) |

(52) U.S. Cl.
CPC ........ *G01M 15/102* (2013.01); *G01N 1/2252* (2013.01); *F01N 2450/10* (2013.01)

(58) Field of Classification Search
CPC . F01N 2450/10; G01M 15/102; G01N 1/2252
See application file for complete search history.

(56) References Cited

U.S. PATENT DOCUMENTS

| | | | | |
|---|---|---|---|---|
| 3,653,115 | A * | 4/1972 | Perkins | F16L 1/09 |
| | | | | 254/29 R |
| 4,373,377 | A | 2/1983 | Smith et al. | |
| 4,779,904 | A * | 10/1988 | Rich | B08B 15/002 |
| | | | | 277/355 |
| 4,786,087 | A | 11/1988 | Thewlis et al. | |
| 5,022,137 | A | 6/1991 | Sorensen et al. | |
| 5,907,109 | A | 5/1999 | Tedeschi | |
| 6,658,711 | B1 * | 12/2003 | Benson | B25B 5/068 |
| | | | | 269/3 |
| 6,775,890 | B2 * | 8/2004 | Kolarik | B25B 27/10 |
| | | | | 285/114 |
| 7,455,576 | B1 * | 11/2008 | Flataker | A22C 29/046 |
| | | | | 452/16 |
| 7,735,813 | B2 | 6/2010 | Geier et al. | |
| 7,946,160 | B2 | 5/2011 | LaPree et al. | |

(Continued)

FOREIGN PATENT DOCUMENTS

FR     2776496 A1 * 10/1999 ........... B08B 15/002

*Primary Examiner* — Benjamin F Fiorello
(74) *Attorney, Agent, or Firm* — Christopher G. Darrow; Darrow Mustafa PC

(57) ABSTRACT

Systems and methods are provided for temporarily coupling an emission sampling device to a vehicle. The system may include an adaptor having a body and a conduit secured to a body. The conduit may define a coupling portion for connection to a source of emissions. An extension arm may be provided movably coupled to the body, including a gripping end configured to align with and grippingly engage a structure of the vehicle. A drive mechanism may be provided for displacing the extension arm with respect to the body. The gripping end of the extension arm may cooperate with the structure of the vehicle and the drive mechanism to exert a compressive force between the coupling portion of the conduit and the source of emissions.

20 Claims, 3 Drawing Sheets

(56) References Cited

U.S. PATENT DOCUMENTS

| | | | | |
|---|---|---|---|---|
| 8,695,200 | B2* | 4/2014 | Rakowicz | F16L 35/00 |
| | | | | 29/450 |
| 9,470,338 | B2* | 10/2016 | Bouchard | F16L 1/09 |
| 9,573,259 | B1* | 2/2017 | Elsasser | B25B 27/10 |
| 2005/0121842 | A1* | 6/2005 | Lo | B25B 5/068 |
| | | | | 269/6 |
| 2007/0176342 | A1* | 8/2007 | Noniewicz | B25B 5/068 |
| | | | | 269/6 |
| 2012/0248759 | A1* | 10/2012 | Feith | B25B 27/10 |
| | | | | 285/39 |
| 2013/0047389 | A1* | 2/2013 | Eldar | B25B 27/10 |
| | | | | 29/237 |

* cited by examiner

QUICK CONNECT TESTING JIG

TECHNICAL FIELD

The present disclosure generally relates to a connector for vehicle emissions testing, and more particularly, to a quick connect testing jig or adaptor for removably coupling a testing or sampling device to an emissions outlet.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Performing a mass flow analysis on exhaust emissions of an engine is often beneficial for diagnosing certain performance issues, as well as for measuring amounts of particulate that may be present in an engine exhaust stream. The integrity of an exhaust emissions sample is an important aspect for the proper testing and measurement of emissions. With certain tests, for example, it is desirable that emission samples are not diluted with ambient air. Thus, an appropriately sealed connection is needed between a source of emissions and any testing equipment.

For vehicles, typical variations in the geometry, profile, and/or tail pipe diameter of an exhaust system may pose problems with respect to the use of a universal adaptor or connection member between a source of exhaust emissions and an emission sampling device or test unit. Further, many vehicles may be provided with optional OEM, aftermarket, or custom exhaust tips for aesthetic or acoustic purposes, which additionally vary the exterior dimensions, making a universal direct connection more difficult.

Accordingly, it would be desirable to provide an improved quick connect testing jig or adaptor for removably coupling a wide variety of vehicle emissions outlets with various testing equipment.

SUMMARY

This section provides a general summary of the disclosure, and is not a comprehensive disclosure of its full scope or all of its features.

In various aspects, the present teachings provide an adaptor assembly for coupling a source of emissions to a testing unit. The adaptor may include a body and a cylindrical conduit configured to direct a flow of emissions. The conduit may be secured to the body, defining a coupling portion for connection to the source of emissions. An extension arm may be provided movably coupled to the body and including a gripping end. A drive mechanism may be provided to displace the extension arm with respect to the body.

In other aspects, the present teachings provide a system for coupling an emission sampling device to a vehicle. The system may include an adaptor having a body and a conduit secured to the body. The conduit may define a coupling portion for connection to a source of emissions. An extension arm may be provided movably coupled to the body, including a gripping end configured to align with and grippingly engage a structure of the vehicle. A drive mechanism may be provided for displacing the extension arm with respect to the body. The gripping end of the extension arm may cooperate with the structure of the vehicle and the drive mechanism to exert a compressive force between the coupling portion of the conduit and the source of emissions.

In still other aspects, the present teachings provide a method of temporarily coupling an emission sampling device to a vehicle for emissions testing. The method may include aligning an adaptor assembly with an exhaust pipe of the vehicle. The adaptor assembly may have a body, a conduit coupled to the body, an extension arm having a gripping end, and a drive mechanism. The method may include inserting the conduit at least partially into the exhaust pipe, and aligning the gripping end of the extension arm with a structural support member of the vehicle. The drive mechanism then may be engaged to displace the gripping end of the extension arm in a direction toward the body, thereby exerting a compressive force between the coupling portion of the conduit and the interior of the exhaust pipe. Upon completion of emissions collections, the method may include selectively releasing the compressive force and disengaging the conduit from the exhaust pipe.

Further areas of applicability and various methods of enhancing the above coupling technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein.

Figure 1:
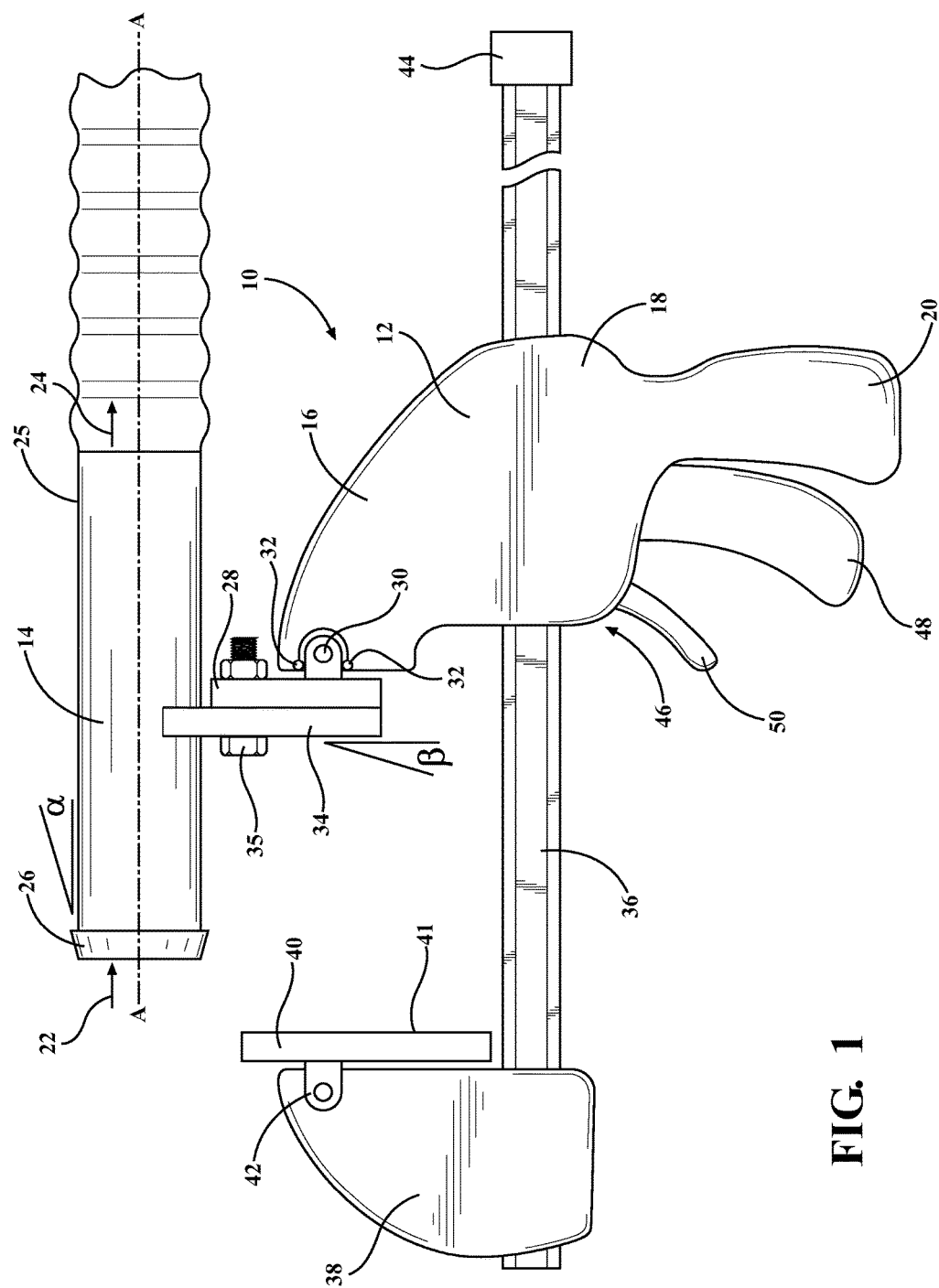
FIG. 1 is a side plan view of an exemplary adaptor assembly for coupling a source of emissions to a testing unit according to various aspects of the present teachings.

It should be noted that the figures set forth herein are intended to exemplify the general characteristics of materials, methods, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DETAILED DESCRIPTION

The following description is merely illustrative in nature and is in no way intended to limit the disclosure, its application, or uses. As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

Various purposes of a vehicle exhaust system include transferring exhaust gas from the engine combustion process away from the passenger compartment, cleaning the exhaust gas of various pollutants and toxic gases, and softening the sounds of the engine. Hydrocarbons and other emissions/particulates present in the exhaust gas may be subject to various regulations concerning both their content and their amount. Certain regulations involve in-use testing. Almost all automotive vehicle exhaust systems include a small elongated steel structure, commonly known as a muffler, that reduces the power of sound waves to help soften and quiet the exhaust. The muffler typically includes one or more tailpipe or exhaust pipe protruding therefrom.

The present technology generally concerns adaptors or jigs useful in collecting and/or directing vehicle emissions for testing or sampling. More specifically, the present technology relates to a universal-type adaptor device for temporarily coupling a source of emissions from a vehicle, such as an exhaust pipe, to an emission sampling device or other testing unit.

As used herein, the term "vehicle" should be construed having a broad meaning, and should include all types of vehicles, with non-limiting examples including a passenger or commercial automobile, car, truck, motorcycle, off-road vehicle, bus, boat, airplane, helicopter, lawn mower, recreational vehicle, amusement park vehicle, farm vehicle, construction vehicle, tram, golf cart, train, or trolley, etc.

In various non-limiting aspects, the present technology provides an adaptor assembly for coupling a source of emissions to a testing unit. FIG. 1 illustrates a side plan view of an exemplary adaptor 10. As shown, the adaptor 10 may include a body 12 and a longitudinally extending conduit 14 coupled to the body 12 and configured to direct a flow of emissions.

Non-limiting examples of the body 12 may be metal, plastic, or a combination thereof, and have a variety of shapes, including an upper area 16 and a lower area 18 having a handle member 20 extending therefrom. In one non-limiting example, the body 12 may include two molded clam-shell type components that may be mechanically or otherwise joined to one another and providing a hollow, or partially hollow, interior. The body 12 may define various apertures to accommodate other structural components and features, as will be described in more detail below.

In various aspects, the conduit 14 may be substantially cylindrical in shape, and generally includes an inlet area 22 and a spaced apart outlet area 24, typically aligned with one another on a longitudinal axis "A." The conduit 14 is preferably made from a rigid, heat resistant material, such as stainless steel, that can sustain compressive forces and extended contact with a vehicle exhaust gas. The inlet 22 and the outlet 24 may define openings that have a similar cross-sectional area such that there is little or no pressure differential through the conduit 14. In certain aspects, it may be desirable that the outlet 24 opening is slightly larger than the inlet 22 opening. Although the inlet 22 and the outlet 24 may have various shapes, a substantially circular opening may allow for a more universal connection to other components. It should be understood that the shape of the inlet 22 and the outlet 24 should substantially match the shape of the respective components to which they will be attached. For example, if it is desirable to connect to a substantially oval shaped exhaust pipe, the inlet 22 should be provided with an appropriate oval shape.

It is also envisioned that the adaptor assembly 10 of the present teachings may be provided as a kit including more than conduit 14 for connection to the body 12. For example, multiple conduits may be provided having different lengths, inlet and outlet shapes, or other design configurations that may be specific to a specialized and/or certain type of exhaust system, muffler, or exhaust pipe.

Figure 2:
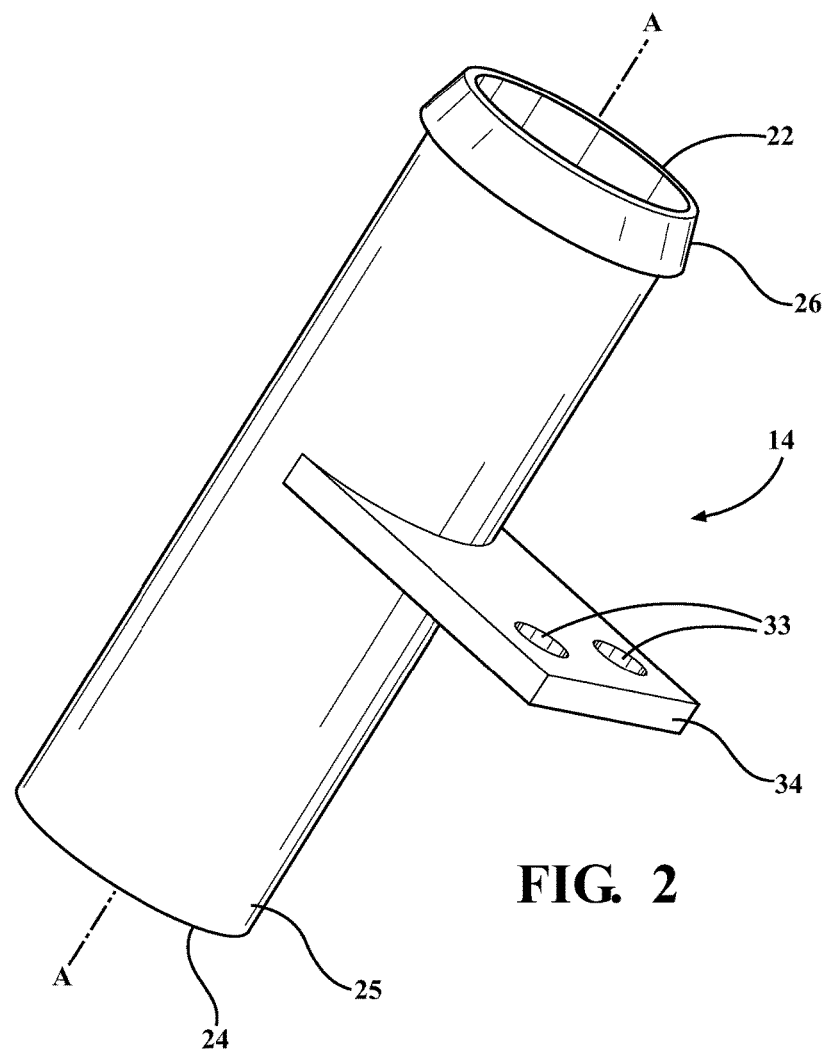
FIG. 2 is bottom perspective view of a conduit member of the adaptor as shown in FIG. 1.

FIG. 2 illustrates a bottom perspective view of the conduit 14 member of the adaptor 10 as shown in FIG. 1. In various aspects, the conduit 14 may define a coupling portion 26 adjacent the inlet 22 for the connection to a source of emissions, such as an exhaust pipe. As shown in FIGS. 1 and 2, the coupling portion 26 may include an outwardly extending frustoconical surface, such as an end having a tapered edge or an angled profile. In certain aspects, the taper can be provided having an angle alpha ($\alpha$) of from about 5 to about 30 degrees, from about 10 to about 25 degrees, or about 20 degrees with respect to the longitudinal axis "A" of the conduit 14.

It is envisioned that the coupling portion 26 allows for the conduit 14 to substantially form an airtight seal with an interior portion of the exhaust pipe, as discussed in more detail below. Although not specifically shown in detail, the area of the conduit adjacent the outlet 24 designated by reference number 25 of FIG. 1 may also be provided with a coupling portion similar to the inlet 22. Alternatively, it may be desirable to provide the outlet 24 with an appropriate fitting, threads, and/or a plug design for connection to a tube, hose, or similar connector ultimately in fluid communication with the emissions testing, collection, or sampling device.

Figure 3:
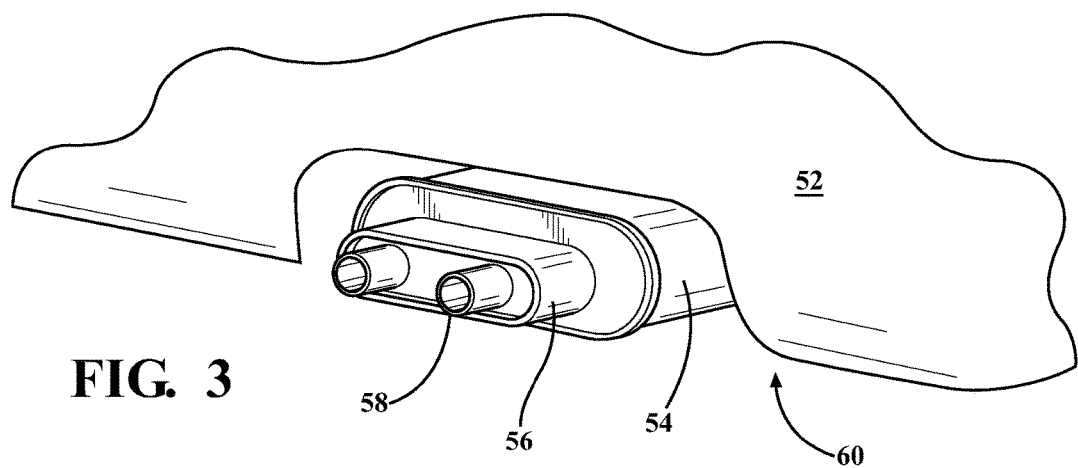
FIG. 3 is a partial perspective view of a region of an exemplary exhaust system of a vehicle, including a muffler.
Figure 4:
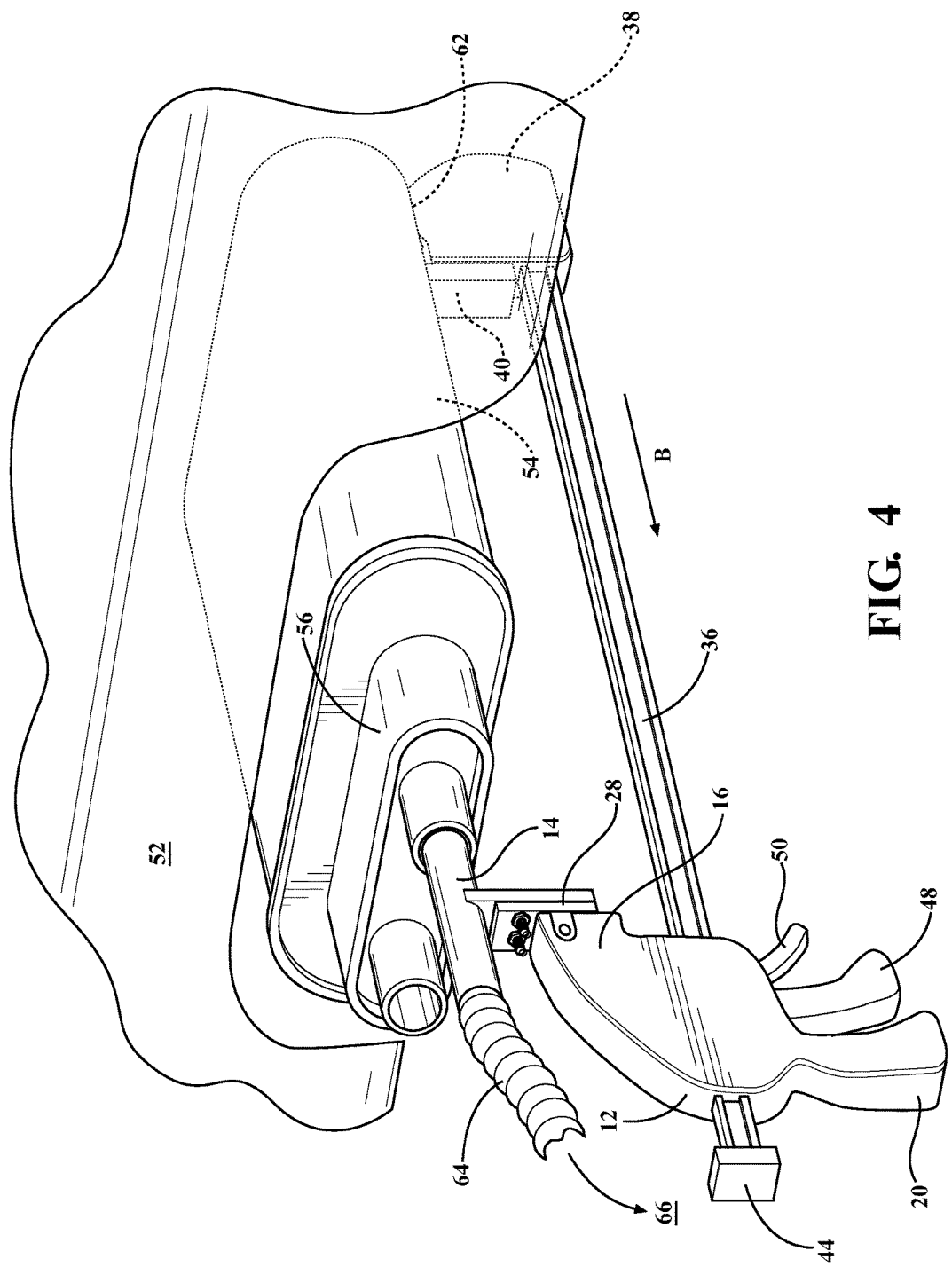
FIG. 4 is the partial perspective view of FIG. 3 illustrating the adaptor connecting an exhaust pipe to an emissions testing device.

The conduit 14 may be hingedly or pivotally secured to an upper area 16 of the body 12. This configuration allows for limited movement of the conduit 14 with respect to the body 12 in order to assist the alignment of the conduit 14 and a source of emissions, such as an exhaust pipe (FIGS. 3-4). As shown, a connecting member 28 may ultimately be attached to the upper area 16 of the body 12 with a hinge pin 30, or a similar type of mechanical fastener to allow rotational movement, such as a rivet, bolt, or the like. Suitable stop pins 32 may be provided to limit the rotational movement. Additionally or alternatively, the body 12 may be formed having a shape configured to limit or restrict movement of the connecting member 28. In certain aspects, the connection permits a pivotal (both forward or rearward) movement of the conduit 14 at an angle (β) of from about 5 to about 25 degrees, from about 10 to about 20 degrees, or up to about 15 degrees with respect to the fixed body 12. In various aspects, for example when working with a turn-down exhaust tip or a tip with an oval shape, the angle of (β) may need to be increased in order to accommodate the different shape or angle of approach.

The conduit 14 may include an extension member 34 for attachment purposes, extending in a substantially orthogonal direction from the conduit 14 as shown in FIGS. 1 and 2. The extension member 34 may be flat or otherwise shaped having a length and width commensurate to match a shape of the connecting member 28. In various aspects, the extension member 34 is welded to the conduit 14. The extension member 34 may be provided with, or otherwise define, one or more apertures 33 to accept a mechanical fastener 35, or the like, for coupling the extension member 34 of the conduit 14 to the connecting member 28 of the body 12.

An extension arm 36 may be provided movably coupled to or within the body 12 and including a gripping end 38 and an opposing stopping end 44 configured to prevent the extension arm 36 from being detached from the body 12. As shown, the extension arm is generally disposed within a bore located in a central region of the body 12, or other region as desired. It should be understood that the extension arm 36 could also be coupled to an exterior portion of the body 12 (not shown). The gripping end 38 of the extension arm 36 may include a contact pad 40.

In various aspects, the contact pad 40 defines a major area/surface 41 disposed substantially perpendicular to the longitudinal axis "A" of the conduit 14. The coupling area/surface 41 may provide a heat resistant, non-slip clamping surface configured to engage a substantially rigid portion of the vehicle. For example, the contact pad 40 may be configured to engage with a structure of the vehicle frame, or a portion of the exhaust system, such as a muffler, as will be described in more detail below. In other aspects, the contact pad 40 may be rigid, or include certain hook, depression, and/or retaining features to grasp or grippingly engage a structural component. The contact pad 40 may be removably coupled or permanently fixed to the gripping end 38 of the extension arm 36. Optionally, the contact pad 40 or an attachment portion 42 may also be pivotally coupled to the gripping end 38.

A drive mechanism 46 may be provided to displace the extension arm 36 along its longitudinal axis with respect to the body 12. Details of exemplary drive mechanisms useful with the present disclosure can be found in U.S. Pat. Nos. 5,022,137, and 7,735,813, each of which is incorporated herein by reference in its entirety. In various aspects, the drive mechanism 46 may include a ratcheting trigger 48 and a suitable release lever 50. Engagement of the ratcheting trigger 48 initiates a displacement of the gripping end 38 of the extension arm 36 in a direction toward the body 12. When the conduit 14 is coupled to an exhaust pipe, the displacement preferably exerts a compressive force between the coupling portion 26 of the conduit 14 and the interior of the exhaust pipe. The release lever 50 is provided for loosening the compressive force.

In other aspects, the present teachings provide a system for coupling an emission sampling device to a vehicle. FIG. 3 is partial perspective view of a region of an exemplary exhaust system of a vehicle 52, including a muffler 54. As shown, the muffler 54 may include one more extensions 56 with an exhaust pipe 58 disposed therein. Generally, exhaust pipes 58 are provided with a substantially circular discharge opening. However, the extensions 56, if present, may vary in size, shape, and placement in relation to the exhaust pipe 58. In order to accommodate such various designs, the present teachings couple the inlet 22 of the conduit 14 of the adaptor assembly 10 within an interior surface of the exhaust pipe 58, as opposed to coupling with an exterior surface of the exhaust pipe 58, which could be obstructed based on any extensions 56 or the exterior shape of the exhaust pipe 58.

FIG. 4 is the partial perspective view of FIG. 3, further illustrating the adaptor assembly 10 connecting a source of emissions, such as the exhaust pipe 58, to a hose 64 in fluid communication with an emissions testing and/or sampling device 66, or other sample collection apparatus. It should be understood that various hoses and connection systems may be used to ultimately couple the conduit 14 with the emissions testing device 66 and the details of such connections may vary as desired.

The system may include an adaptor 10 having a body 12 and a conduit 14 secured to the body 12, as described above. The extension arm 36 may be provided movably coupled to the body 12, including a gripping end 38 configured to align with and grippingly engage a structural support member or feature of the vehicle 52. In one example, the gripping end 38 and/or contact pad 40 may be aligned with or adjacent to a portion of the vehicle frame, a part of which may be generally located near the muffler of the exhaust system and depicted by reference number 60 of FIG. 3. In another example, the gripping end 38 and/or contact pad 40 may be aligned with or adjacent a distal end 62 of the muffler 54 of the vehicle 52.

In still other aspects, the present teachings provide a method of temporarily coupling a sampling collection device 66 to a vehicle 52 during emissions testing. Where a kit including a plurality of different conduits are provided, the method may begin with selecting and appropriate conduit 12 and coupling the conduit to the body 12 of the adaptor assembly 10. The method may include aligning an adaptor assembly 10 with an exhaust pipe 58 or tailpipe of the vehicle 52. As described above, one exemplary adaptor assembly 10 may have a body 12, a conduit 14 coupled to the body 12, an extension arm 36 having a gripping end 38, and a suitable drive mechanism 46. The method may initially begin with aligning and inserting the conduit 14 at least partially into the exhaust pipe 58. In various aspects, and depending upon whether the muffler 54 includes any extensions 56, this may include pivoting the conduit 14 between about 10 to about 20 degrees with respect to the body 12 prior to inserting a tapered edge 26 of the conduit 14 into an interior region of the exhaust pipe 58.

The method may continue with aligning the gripping end 38 and/or contact pad 40 of the extension arm 36 with a structural support member of the vehicle, as described above. This may include engaging the release lever 50 in order to lengthen the extension arm 36. Once aligned, the drive mechanism 46 may be engaged via the ratcheting trigger 48. Repeated actuation of the ratcheting trigger 48 displaces the gripping end 38 of the extension arm 36 in a direction toward the body as noted by arrow "B" of FIG. 4, thereby exerting a compressive force between the coupling portion 26 of the conduit 14 and the interior of the exhaust pipe 58. It should be understood that the outlet 24 of the conduit 14 may be coupled to the hose 64 or other connection means in ultimate fluid communication with the testing device 66 at various points during the method.

Upon completion of emissions collections or testing, the method may include selectively releasing the compressive force by engaging the release lever 50 coupled to the drive mechanism 46, extending the arm 36, and then disengaging the conduit 14 from the exhaust pipe 58.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

What is claimed is:

1. An adaptor assembly for coupling a source of emissions to a testing unit, the adaptor comprising:
    a body;
    a conduit configured to receive and direct a flow of emissions between the source of emissions and the testing unit, the conduit comprising an extension member extending therefrom and secured to the body, the conduit defining a coupling portion for connection to the source of emissions;
    an extension arm movably coupled to the body and including a gripping end; and
    a drive mechanism for displacing the extension arm with respect to the body.

2. The adaptor assembly of claim 1, wherein the source of emissions is an exhaust pipe of a vehicle and the coupling portion of the conduit defines a tapered edge profile to sealingly engage with an interior of the exhaust pipe.

3. The adaptor assembly of claim 2, wherein the tapered edge profile is angled from about 15 to about 25 degrees with respect to a longitudinal axis of the conduit and creates an airtight seal between the conduit and the exhaust pipe.

4. The adaptor assembly of claim 2, wherein the drive mechanism comprises:
    a ratcheting trigger to initiate a displacement of the gripping end of the extension arm in a direction toward the body and exert a compressive force between the coupling portion of the conduit and the interior of the exhaust pipe; and
    a release lever for loosening the compressive force.

5. The adaptor assembly of claim 1, wherein the extension member of the conduit is pivotally coupled to the body, allowing a pivotal movement of the conduit from about 10 to about 20 degrees with respect to the body.

6. The adaptor assembly of claim 1, wherein the gripping end of the extension arm comprises a contact pad providing a heat resistant, non-slip clamping surface, the contact pad defining a major surface disposed substantially perpendicular to a longitudinal axis of the conduit.

7. The adaptor assembly of claim 1, wherein the conduit comprises a stainless steel elongated cylinder.

8. A system for coupling an emission sampling device to a vehicle, the system comprising:
    an adaptor including:
        a body;
        a conduit comprising an extension member extending therefrom and secured to the body, the conduit defining a coupling portion for connection to a source of emissions from the vehicle:
        an extension arm movably coupled to the body and including a gripping end configured to align with and grippingly engage a structure of the vehicle; and
    a drive mechanism for displacing the extension arm with respect to the body,
    wherein the gripping end of the extension arm cooperates with the structure of the vehicle and the drive mechanism to exert a compressive force between the coupling portion of the conduit and the source of emissions.

9. The system of claim 8, wherein the source of emissions is an exhaust pipe and the coupling portion of the conduit defines a tapered edge profile to sealingly engage with an interior of the exhaust pipe.

10. The system of claim 9, wherein the tapered edge profile is angled from about 15 to about 25 degrees with respect to a longitudinal axis of the conduit and creates an airtight seal between the conduit and the exhaust pipe.

11. The system of claim 8, wherein the gripping end comprises a heat resistant, non-slip contact pad configured to be clamped to a muffler of the vehicle.

12. The system of claim 8, wherein the extension member of the conduit is pivotally coupled to the body, allowing a pivotal movement of the conduit from about 10 to about 20 degrees with respect to the body.

13. A method of temporarily coupling a sampling device to a vehicle for emissions testing, the method comprising:
    aligning an adaptor assembly with an exhaust pipe of the vehicle, the adaptor assembly comprising a body, a conduit comprising an extension member that is coupled to the body, an extension arm having a gripping end, and a drive mechanism;
    inserting the conduit at least partially into the exhaust pipe;
    aligning the gripping end of the extension arm with a structural support member of the vehicle; and
    engaging the drive mechanism and displacing the gripping end of the extension arm in a direction toward the body, thereby exerting a compressive force between a coupling portion of the conduit and an interior of the exhaust pipe.

14. The method of claim 13, wherein the conduit defines a tapered edge profile and the method comprises pivoting the conduit with respect to body prior to inserting the tapered edge of the conduit at least partially into the exhaust pipe.

15. The method of claim 14, comprising:
    pivoting the conduit between about 10 to about 20 degrees with respect to the body; and
    aligning the tapered edge of the conduit with an interior of the exhaust pipe.

16. The method of claim 14, wherein aligning the gripping end with a structural support member of the vehicle comprises aligning the gripping end adjacent a distal end of a muffler of the vehicle.

17. The method of claim 14, wherein aligning the gripping end with a structural support member of the vehicle comprises aligning the gripping end adjacent a vehicle frame.

18. The method of claim 14, wherein engaging the drive mechanism and displacing the gripping end of the extension arm comprises actuating a ratcheting trigger extending from the body.

19. The method of claim 13, further comprising:
    selectively releasing the compressive force upon completion of emissions collections; and
    disengaging the conduit from the exhaust pipe.

20. The method of claim 19, wherein selectively releasing the compressive force comprises engaging a release lever coupled to the drive mechanism.

\* \* \* \* \*